(12) United States Patent
Gielen et al.

(10) Patent No.: US 8,818,525 B2
(45) Date of Patent: Aug. 26, 2014

(54) LEAD HAVING THIN DISTAL END PORTION

(75) Inventors: Frans L H Gielen, Eckelrade (NL); Peter Appenrodt, Bremen (DE); Paulus van Venrooij, Hoensbroek (NL)

(73) Assignee: Medtronic, Inc., Minneapolis, MN (US)

( * ) Notice: Subject to any disclaimer, the term of this patent is extended or adjusted under 35 U.S.C. 154(b) by 155 days.

(21) Appl. No.: 13/025,580

(22) Filed: Feb. 11, 2011

(65) Prior Publication Data
US 2012/0209364 A1 Aug. 16, 2012

(51) Int. Cl.
*A61N 1/36* (2006.01)

(52) U.S. Cl.
USPC ............................................. 607/116

(58) Field of Classification Search
USPC ............................................. 607/116
See application file for complete search history.

(56) References Cited

U.S. PATENT DOCUMENTS

| | | | |
|---|---|---|---|
| 5,782,760 A * | 7/1998 | Schaer | 600/381 |
| 5,843,148 A * | 12/1998 | Gijsbers et al. | 607/116 |
| 6,597,953 B2 * | 7/2003 | Boling | 607/45 |
| 6,721,604 B1 | 4/2004 | Robinson | |
| 6,952,616 B2 | 10/2005 | Wessman | |
| 7,047,082 B1 * | 5/2006 | Schrom et al. | 607/116 |
| 7,051,419 B2 | 5/2006 | Schrom | |
| 2002/0116042 A1 | 8/2002 | Boling | |
| 2004/0064174 A1 | 4/2004 | Belden | |
| 2004/0111141 A1 * | 6/2004 | Brabec et al. | 607/119 |
| 2005/0228249 A1 | 10/2005 | Boling | |
| 2006/0129203 A1 | 6/2006 | Garabedian | |

OTHER PUBLICATIONS

International Search Report and Written Opinion dated Feb. 21, 2012; PCT/US2011/058531.

* cited by examiner

*Primary Examiner* — Amanda Patton

(57) ABSTRACT

A deep brain stimulation lead includes a distal end portion having a length of greater than 5 millimeters and a largest outer diametric dimension of 1 millimeter or less. One or more electrodes are disposed at the distal end portion. The lead also includes a proximal end portion having one or more contacts electrically coupled to the one or more electrodes. The lead further includes a mid portion between the proximal end portion and the distal end portion. The mid portion has an outer diametric dimension of greater than 1 millimeter and is configured and positioned to be located in proximity to a burr hole of a skull of patient when the distal end portion is positioned in the brain of the patient at a location to deliver a signal to a target region.

18 Claims, 7 Drawing Sheets

LEAD HAVING THIN DISTAL END PORTION

FIELD

This application relates to medical devices; and more particularly to implantable medical leads for applying electrical signals to deep brain structures.

BACKGROUND

Implantable neurostimulators have been used or suggested to treat a variety of neurological diseases. In some cases, electrical signals generated by the neurostimulators are applied to regions or structures of the brain via electrodes of leads operably coupled to the stimulator. Often the brain regions or structures that are targeted are very small. As a result, it can be difficult to properly place a lead such that the signal may be applied to the desired target. In addition, placement of leads having large outer diameters into the brain can cause undesired injury to tissue, which in some cases may be the tissue for which therapy is directed.

BRIEF SUMMARY

The present disclosure describes, among other things, leads that have thin distal ends. Because of the thin distal ends, the leads can be implanted in a patient's brain without causing as much damage as thicker leads. In some cases multiple leads having thin distal ends can be placed in a patient's brain so that the combination of leads can better capture the desired brain region or structure. When multiple leads are placed in a patient's brain, reduced tissue damage associated with thinner leads is further appreciated.

In various embodiments described herein, an implantable deep brain stimulation lead includes a distal end portion having a length of greater than 2 millimeters and a largest outer diametric dimension of 1 millimeter or less. One or more electrodes are disposed at the distal end portion. The lead also includes a proximal end portion having one or more contacts electrically coupled to the one or more electrodes. The lead further includes a mid portion between the proximal end portion and the distal end portion. The mid portion has an outer diametric dimension of greater than 1 millimeter and is configured and positioned to be located in proximity to a burr hole of a skull of patient when the distal end portion is positioned in the brain of the patient at a location to deliver a signal to a target region.

In numerous embodiments described herein, a method for manufacturing a lead includes extending, in a linear manner each of one or more conductors from a proximal portion of a distal end portion of a lead (e.g., the intersection of the distal end portion and the mid portion) to one of one or more electrodes at the distal end portion of the lead. The method further includes (i) electrically coupling each of the one or more conductors to one of the one or more electrodes; and (ii) embedding the one or more conductors in polymeric material such that no luminal void exists between the conductors.

In various embodiments described herein, a method for deep brain stimulation includes inserting a distal end portion of a lead into parenchymal tissue of a brain, wherein the distal end portion of the lead that is inserted into a brain has an outer diameter of 1 millimeter or less and a length of 10 millimeters or more. The method further includes anchoring a mid portion of the lead in proximity to a burr hole in a skull. The mid portion of the lead has an outer diameter of greater than 1 millimeter. The mid portion is immediately proximal to the distal end portion. The distal end portion of the lead accounts for 90% or more of the lead that is inserted into the parenchymal tissue when the lead is properly positioned in the brain.

By using leads having thinner distal ends as described herein, less damage may result from implantation of such leads relative to conventional deep brain stimulation leads. Due in part to the reduction in damage, more leads may be implanted to ensure that the target brain region is appropriately captured. In addition, the leads described herein may include a thicker more proximal mid sections that provide for sufficient robustness and structural integrity; e.g., to allow for proper anchoring of the lead with a burr hole cap anchor or for mechanical forces that may be imposed by bending or stretch. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "proximal" and "distal" refer to position relative to an implantable electrical medical device. For example, a proximal portion of a lead is a portion nearer an implantable electrical medical device, and a distal portion is a portion further from the implantable electrical medical device.

The present disclosure relates to, among other things, leads that have thin distal ends. Because of the thin distal ends, the leads can be readily implanted in a patient's brain. In some cases, multiple leads having distal ends can be placed in a patient's brain so that the combination of leads can better capture the desired brain region or structure. When multiple leads are placed in a patient's brain, advantages associated with reduced volume of thinner leads is further appreciated. While advantages of the leads may be well appreciated when used for deep brain stimulation, the leads described herein may be used for any suitable purpose with any suitable system.

Figure 1:
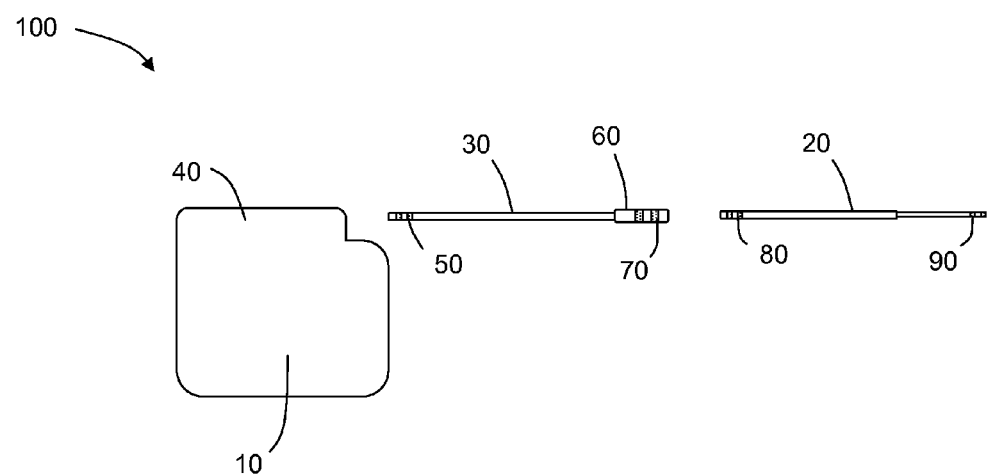
FIG. 1 is a schematic side view of an implantable electrical signal generator system.

An overview of an exemplary system is depicted in FIG. 1. The system 100 includes an implantable electrical device 10. Electrical device 10 may be any electrical signal generator or receiver useful for delivering therapy to a patient or for patient diagnostics. For example, electrical device 10 may be a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. The system 100 also includes a lead 20 and a lead extension 30 for operably coupling the lead 20 to the electrical device 10. In some embodiments, the lead 20 may be directly coupled to the device 10 without the need for an extension 30. While not shown, it will be understood that more than one lead 20 may be operably coupled to one electrical device 10 or one extension 30 or that more than one extension 30 may be operably coupled to one electrical device 10.

Still referring to FIG. 1, the depicted implantable electrical device 10 has a connector block 40 configured to receive proximal end of extension 30, which includes contacts 50 configured to couple to internal contacts in header 40. The distal end of extension 30 comprises a connector 60 configured to receive proximal end of lead 20. Connector 60 has internal electrical contacts 70 that are electrically coupled to the proximal contacts 50. The internal contacts 70 of the connector 60 are configured to electrically couple extension 30 to lead 20 via electrical contacts 80 disposed on the proximal end portion of lead 20. Electrodes 90 are disposed on distal end portion of lead 20 and are electrically coupled to electrical contacts 80 through conductors (not shown). Lead 20 may include any number of electrodes 90, e.g. one, two, three, four, five, six, seven, eight, sixteen, thirty-two, or sixty-four. Typically, each electrode 90 is electrically coupled to a discrete electrical contact 80.

Figure 2:
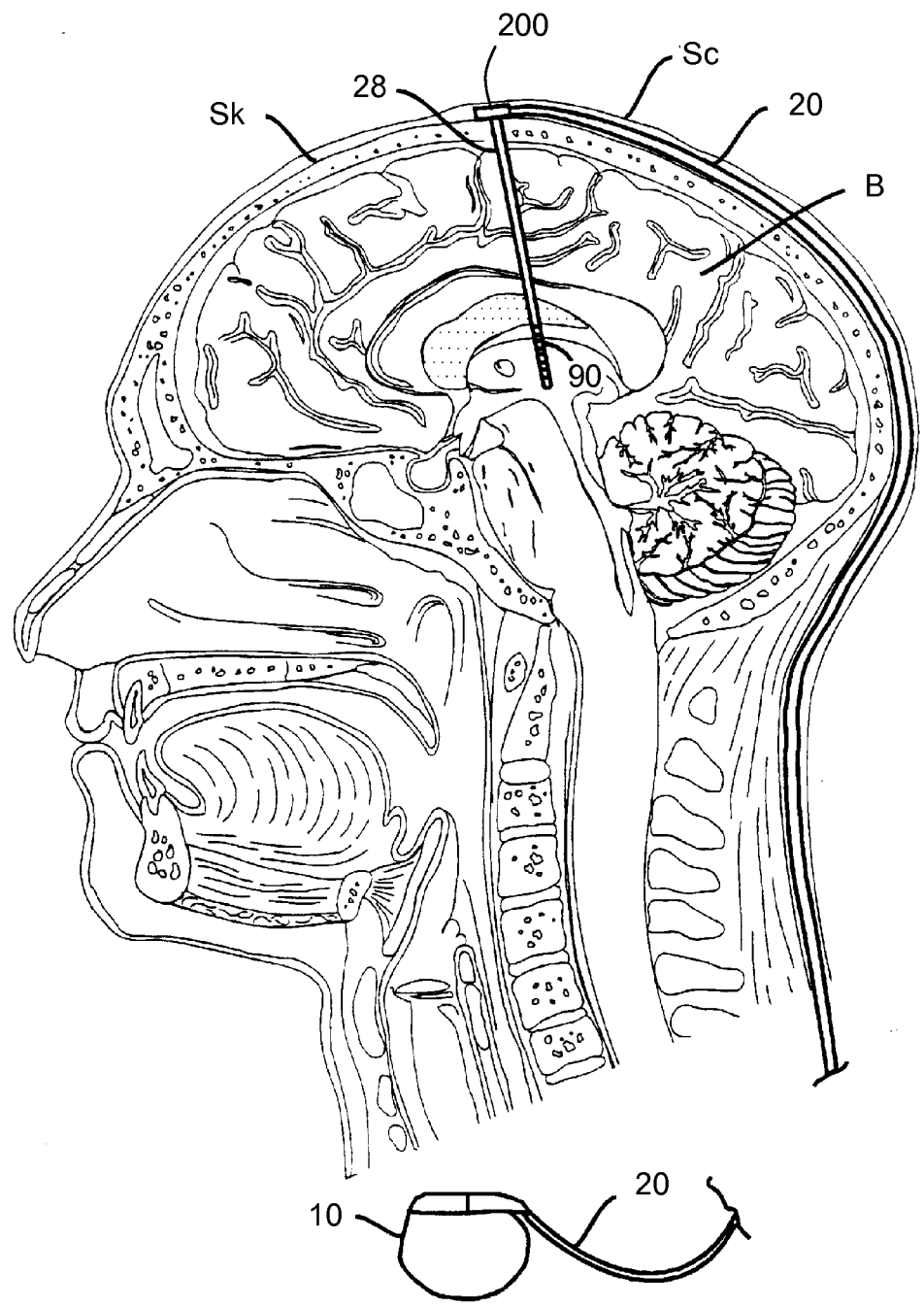
FIG. 2 is schematic view of an implantable electrical signal generator system implanted in a patient, where a distal portion of a lead is implanted in the patient's brain.

As indicated above, the leads described herein (see, e.g., FIGS. 3-10 below) may be particularly advantageous for deep brain stimulation. Referring now to FIG. 2, a system implanted in a patient for purposes of brain stimulation is shown. The system includes a lead 20 operably coupled to an electrical signal generator 10, such as a neurostimulator. The neurostimulator 10 may be implanted in any suitable location of the patient, such as in the pectoral region, the buttocks, or the abdomen. The lead 20 (or lead extension—not shown in the depicted embodiment) may be tunneled subcutaneously between the device 10 and a burr hole in the patent's skull (Sk), with a portion of the lead 20 tunneled between the patient's scalp (Sc) and skull (Sk). A distal portion 28 of the lead that contains electrodes 90 is located in the patient's brain (B). The lead may be placed using stereotactic techniques as known in the art. A burr hole cap anchor 200 engages and secures the lead 20 as it exits the brain (B). Any suitable burr hole cap anchor, such as those disclosed in U.S. Pat. Nos. 6,321,104; 5,464,446; 7,766,922; 7,479,146, 5,954,687; or the like; or available from commercial sources such as Medtronic, Inc. or the like, may be employed. Of course, anchors other than burr hole cap anchors may be employed to engage and retain the lead.

The portion of the lead 20 that is engaged and secured by an anchor, such as the depicted burr hole cap anchor 200, should be sufficiently robust, having sufficient structural integrity to withstand strain placed on the lead at the point or area of capture. The lead 20 proximal to the portion secured in the anchor 20 is typically subjected to a good deal of strain due to, for example, movement of the patient's head and neck or scratching of the scalp during the wound healing process which typically causes itching. To the extent that the lead 20 is held securely in the anchor 200, the portion of the lead distal to the burr hole cap anchor 200 is not subject to much strain, as the distal portion 28 of the lead is fixed relative to the patient's brain (B).

Figure 3:
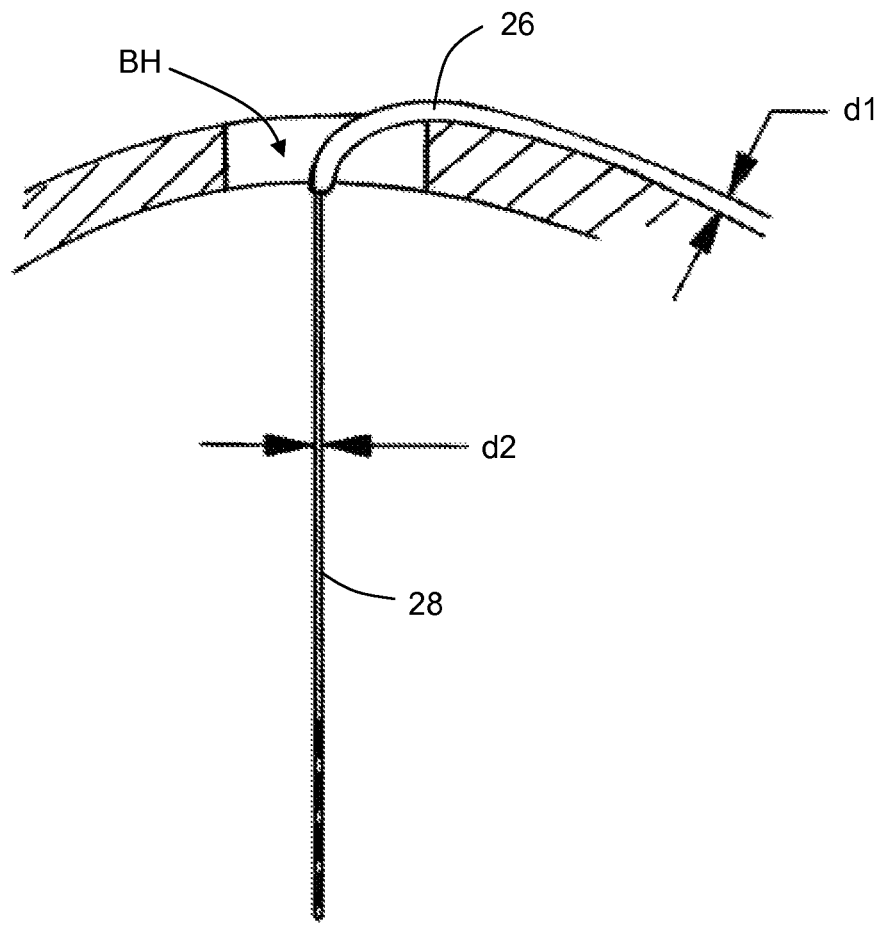
FIG. 3 is a schematic close up view of a lead passed through a burr hole of a skull with a distal portion of the lead inserted in the brain.

Referring now to FIG. 3, a portion of a representative lead is shown. The lead has a distal portion 28 with a diameter d2 that is smaller than a mid portion 26 proximal the distal portion 28. The mid portion 26 has an outer diameter d1 and is constructed to have sufficient strength to be captured by a burr hole (BH) cap anchor (not shown) and withstand strain caused by pulling of the lead proximal to the mid portion 26. The smaller diameter (d2) of the distal portion 28 allows the lead to be inserted into the patient's brain without causing as much damage to parenchymal tissue as it would if the diameter were larger. This can allow for close placement of more than one lead in a patient's brain.

In various embodiments, the distal end portion 28 has a largest outer diametric dimension (d2) of less than 1 millimeter, such as between about 0.1 mm and 1 mm, between about 0.5 mm and 1 mm, or about 0.7 mm. In many embodiments the outer diametric dimension of the distal portion is uniform. As used herein "uniform" with regard to an outer diametric dimension means that the dimension does not change by more than 10% along at least 90% of the length of the distal portion 28.

In various embodiments, the mid portion 26 of the lead has an outer diametric dimension of greater than 1 millimeter, such as about 1.25 mm. This mid portion may be constructed in a manner the same as, or similar to, currently available deep brain stimulation leads, such as Medtronic, Inc.'s Model 3387 or 3389 DBS lead, or as otherwise generally known in the art.

Preferably, the lead is designed such that the distal portion 28 extends into the brain of a patient to a desired distance while the mid portion 26 does not enter the brain parenchyma but is positioned to be captured by a burr hole anchor. Of course, as brain anatomy varies from person to person, it is not always possible for a lead to be designed and manufactured so that the thin distal portion 28 is inserted in the brain, while the mid portion 26 does not enter the parenchyma, but is positioned to be captured by the anchor. Accordingly, in some embodiments, the lead is configured such that at least 90% of the lead that is in the brain parenchymal tissue is the distal portion 28 (i.e., 10% can be mid portion 26).

The distal portion 28 can be any suitable length so that it can be placed such that electrodes are in proximity to a brain target. This length can readily be measured in using conventional sterotactic planning software, such as Medtronic, Inc.'s FrameLink™ solution. Leads with different lengths of the distal portion may be available in the operating room and the appropriate lead length may be chosen depending on the stereotactic planning of brain target and trajectory through the brain. In many embodiments, the distal portion 28 of the lead has a length of 2 mm or greater, such as 5 mm or greater, 10 mm or greater, 20 mm or greater, 30 mm or greater, 40 mm or greater, 50 mm or greater, 60 mm or greater, 70 mm or greater, 80 mm or greater, 90 mm or greater, or 100 mm or greater.

Referring now to FIGS. 4-10, embodiments of a lead 20 having a thin distal end portion 28 and a thicker mid portion 26 proximal the distal end portion 28 are shown. The distal end portion 28 is configured to be placed in a patient's brain such that one or more electrodes 90 can apply an electrical signal to a target region of the brain. The mid portion 26 is configured to be received by an anchor, such as a burr hole cap anchor, when the distal portion 28 is inserted in the brain. The mid portion 28 is positioned between a proximal end portion 24 and the distal end portion 28. In various embodiments, the proximal end portion 24 and the mid portion 26 have the same outer diameter, and the outer diameter is uniform. The contacts 80 disposed at the proximal portion 24 are electrically coupled to the electrodes 90 at the distal end portion 28 by conductors 300.

Figure 4:
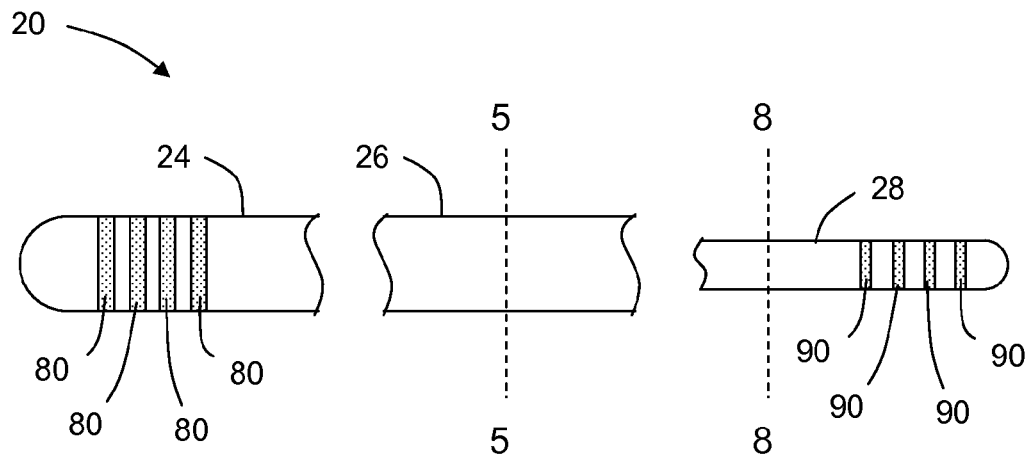
FIG. 4 is a schematic side view of a lead having a thin distal end portion.
Figure 5:
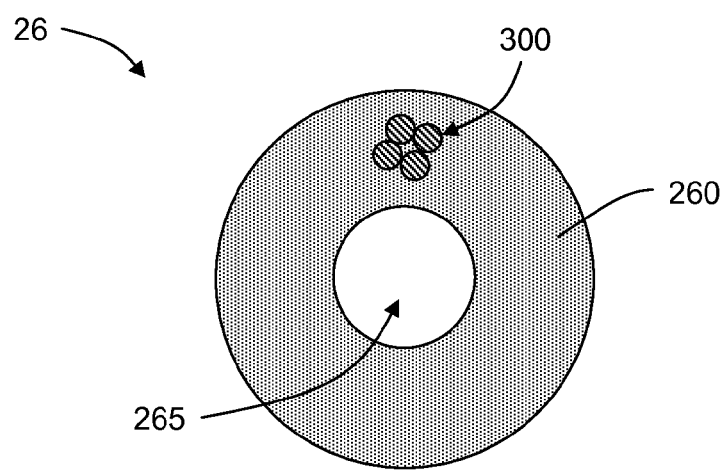
FIG. 5 is a schematic cross sectional view of an embodiment of the lead depicted in FIG. 4, taken through line 5-5.
Figure 6:
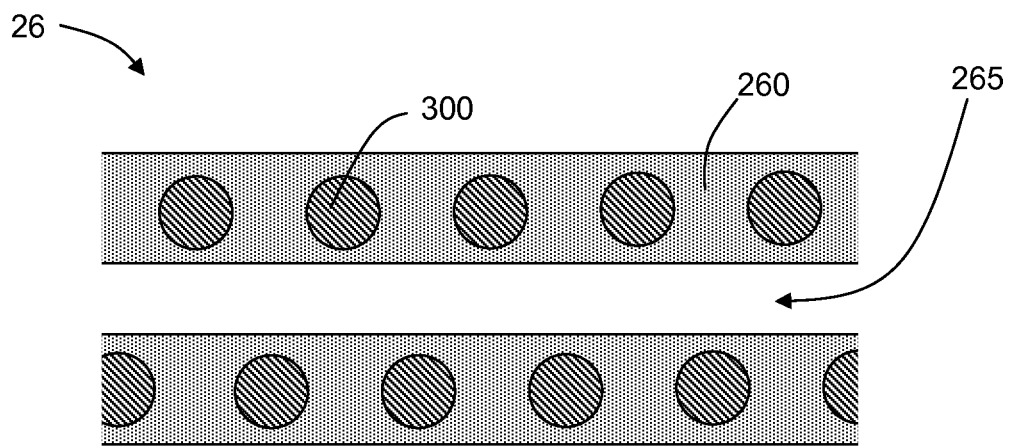
FIG. 6 is a schematic longitudinal sectional view of an embodiment of the mid portion of the lead depicted in FIG. 4.

FIGS. 5-6 show sectional views of the mid portion 26 of one embodiment of the lead depicted in FIG. 4. FIG. 5 is a schematic radial section taken through line 5-5 of FIG. 4; and FIG. 6 is a longitudinal section of the mid portion 26. As shown in FIG. 5-6 the conductors 300 may be bundled together and wrapped around a lumen 265. Typically the bundled conductors are wrapped around tubing having lumen 265 during manufacture of the lead. In embodiments where the lead does not contain a lumen, the bundled conductors 300 may be wrapped around a rod, such as a polymeric rod. In either case, the conductors 300 in the mid portion 26 may be separated by a substantially cylindrical space and may be spirally wound in the mid portion 26. Of course, the conductors in the mid portion may be arranged in any other suitable manner.

Figure 7:
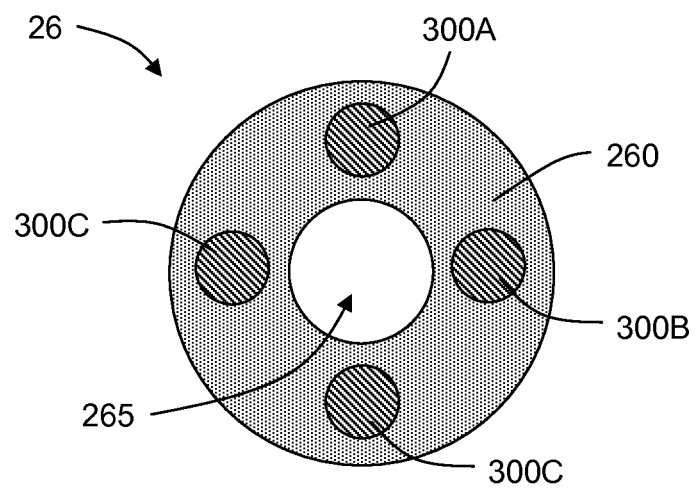
FIG. 7 is a schematic cross sectional view of an alternative embodiment of the lead depicted in FIG. 4, taken through line 5-5.

In the embodiment depicted in FIG. 7. The conductors 300A, 300B, 300C, 300D are not bundled together, but rather are individually wrapped around the lumen 265. The longitudinal sectional view of such a mid portion 26 of a lead would look similar to that depicted in FIG. 6, except that individual conductors rather than bundled conductors are spirally wrapped around the lumen.

Of course, it will be understood that FIGS. 5-7 represent only some options for which the mid portion of the lead may be constructed. The mid portion and the proximal portion of the lead may be constructed in any suitable manner. Similarly the distal portion of the lead may be constructed in any suitable manner such that the outer diameter of the distal portion is smaller than the outer diameter of the mid portion.

Figure 8:
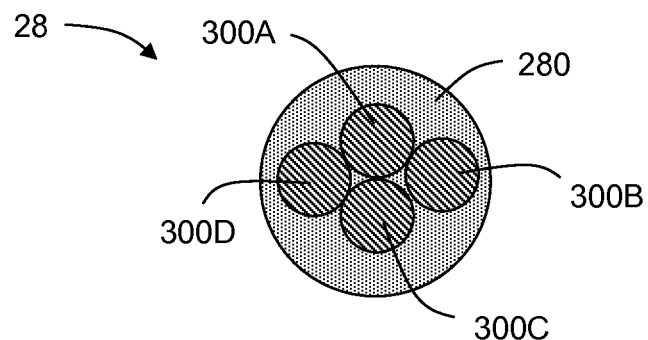
FIG. 8 is a schematic cross sectional view of an embodiment of the lead depicted in FIG. 4, taken through line 8-8.
Figure 9:
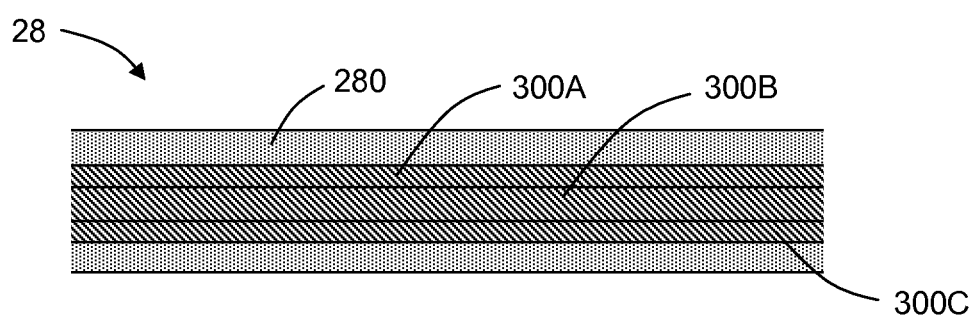
FIG. 9 is a schematic longitudinal sectional view of an embodiment of the distal portion of the lead depicted in FIG. 4
Figure 10:
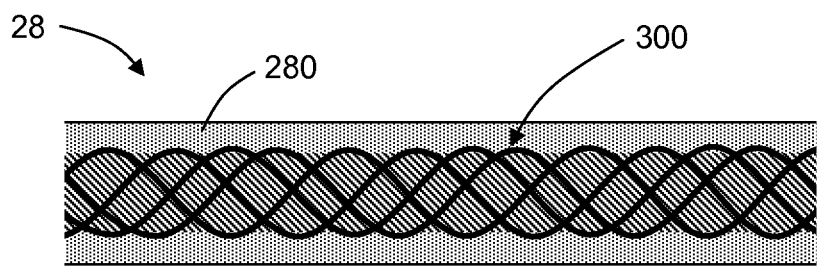
FIG. 10 is a schematic longitudinal sectional view of an alternative embodiment of the distal portion of the lead depicted in FIG. 4.

Referring now to FIGS. 8-10, some example configurations of a distal portion 28 of a lead are shown. In the depicted embodiments, the conductors 300A, 300B, 300C, 300D are straightened out (i.e., not wrapped around a tube or rod) to provide a lumen-less distal portion. By straightening out the conductors and removing the lumen or solid cylindrical portion around which the conductors are wrapped, the overall diameter of the distal end portion may be reduced.

As shown in FIG. 8, which is an embodiment of a schematic cross section taken through line 8-8 of FIG. 4, the space between the individual conductors 300A, 300B, 300C, 300D is reduced or minimized. As shown in the schematic longitudinal section depicted in FIG. 9, the individual conductors 300A, 300B, 300C (conductor 300D is hidden behind the other conductors) run linearly through the lead body 280 along the longitudinal axis of the lead. Alternatively, the individual conductors may be braided or otherwise bundled and the bundled, individually insulated, conductors 300 may be run rectilinearly (rather than spirally) through the lead body 280 as shown in FIG. 10. A radial cross-section of the distal portion 28 of the lead taken through a portion of FIG. 10 would look the same or substantially the same as the schematic section depicted in FIG. 8.

Figure 11:
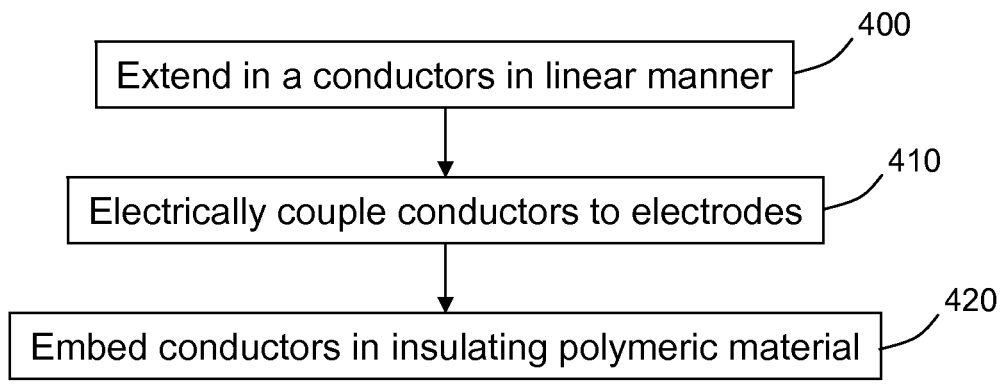
FIG. 11 is a flow diagram depicting an overview of a method described herein.

Distal portions 28 of the lead may be made in any suitable manner. For example and referring to FIG. 11, an overview of a method for making thin distal portions of leads is shown. As discussed above, the conductors may be extended in a linear manner (400). It will be understood that the individual conductors (see, e.g., FIG. 9) or bundled conductors (see, e.g., FIG. 10) may be run linearly, rather than spirally around a tube or rod, to decrease the profile of the distal portion of the lead. The individual conductors are electrically coupled to electrodes (410), and the conductors are embedded in insulating polymeric material (420). It will be understood that the conductors may be embedded in polymeric material before or after being coupled to the electrodes. The polymeric material used can be varied to achieve a desired stiffness of the distal end.

In some embodiments, the conductors are embedded in polymeric material via molding. In some embodiments, the conductors are embedded in polymeric material by placing the conductors in a lumen of a polymeric tube (preferably the inner diameter of the lumen is only slightly larger than the outer diameter of the extended conductors—whether bundled or not), which tube is placed inside of a shrink-wrap sheath, such as a polytetrafluoroethylene or fluorinated ethylene-propylene sheath or tube. The conductor/tube/sheath assembly is heated to reflow the polymer of the tube around the conductors, while the sheath applies a restrictive force to minimize the diameter of the distal end portion of the lead. In some embodiments, the polymer in which the conductors are embedded is polyurethane. In some embodiments, epoxy is used, which may impart a stiffer structure than polyurethane. Of course, any suitable polymer may be used.

In some embodiments, stiffening elements may be included in the distal portion of the lead. For example, rods or fibers of high molecular weight or ultrahigh molecular weight polyethylene, such as Dyneema, may be included in the distal portion of the lead. In some embodiments, the polymeric material in which the conductors are embedded includes a high molecular weight or ultrahigh molecular weight polyethylene, such as Dyneema.

Figure 12:
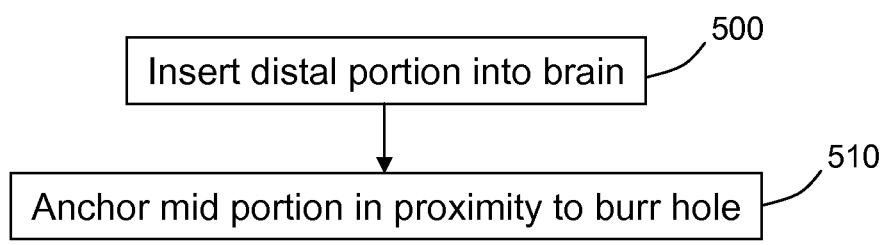
FIG. 12 is a flow diagram depicting an overview of a method described herein.

As discussed above, leads having thin distal end portions and thicker mid portions may be used for any purpose. However, their advantages may be readily realized when the lead is used for deep brain stimulation. An overview of a method associated with deep brain stimulation is depicted in FIG. 12.

The method includes inserting a distal portion of a lead into parenchymal tissue of a brain (500). In many embodiments, at least 90% of the distal portion of the lead that is inserted into a brain has an outer diameter of 1 millimeter or less. The mid portion is anchored in proximity to a burr hole in a skull (510). In many embodiments, the mid portion of the lead has an outer diameter of greater than 1 millimeter.

If the distal portion of the lead is sufficiently stiff, the distal portion may be introduced into the brain directly without use of a guide cannula. In such embodiments, it may be desirable for at least a portion to include a radiopaque or other suitable marker to allow visualization as the distal end is advanced through brain tissue. If use of a guide cannula is desired for stereotactic placement of the lead, the guide cannula preferably has an inner diameter only slightly larger than the outer diameter of the distal portion of the lead to avoid unnecessary damage to brain tissue. In many cases, such a guide cannula will not be able to be readily withdrawn over the thicker mid portion of the lead. To overcome this potential problem, the guide cannula may be in the form of a peelable sheath or the like, which would allow introduction of the distal portion of the lead into the cannula or sheath and would allow removal of the guide cannula or sheath after desired placement of the distal portion of the lead. Of course, any other suitable guide cannula or system may be employed to ensure that the lead is properly positioned.

Thus, embodiments of the LEAD HAVING THIN DISTAL END PORTION are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable brain stimulation lead comprising:
   a distal end portion having a length of 20 millimeters or greater and a largest outer diametric dimension of 1 millimeter or less;
   one or more electrodes disposed at the distal end portion;
   a proximal end portion having one or more contacts electrically coupled to the one or more electrodes; and
   a mid portion between the proximal end portion and the distal end portion, the mid portion having an outer diametric dimension of greater than 1 millimeter and configured and positioned to be located at a burr hole of a skull of a patient when the distal end portion is positioned in the brain of the patient,
   wherein the distal end portion is the only portion extending distally from the mid portion.

2. The lead of claim 1, wherein the distal end portion has a largest outer diametric dimension between 0.1 millimeters and 1 millimeter.

3. The lead of claim 1, wherein the distal end portion has a uniform outer diameter along its length.

4. The lead of claim 1, wherein the lead comprises one or more conductors electrically coupling the one or more electrodes to the one or more contacts, wherein the one or more conductors are spirally wound around a cylindrical space in the mid portion of the lead, and wherein the one or more conductors extend linearly along the longitudinal axis of the lead in the distal end portion.

5. The lead of claim 4, wherein the lead comprises more than one conductor, and wherein, in at least a portion of the distal end portion of the lead, the conductors run linearly through the lead along a longitudinal axis of the lead.

6. The lead of claim 1, wherein the lead comprises more than one individually insulated conductor, each electrically coupling one of the contacts with one of the electrodes, wherein the more than one individually insulated conductors are spirally wound around a cylindrical space in the mid portion of the lead, and wherein, in at least a portion of the distal end portion of the lead, the individually insulated conductors are braided around each other to form a bundled set of individually insulated conductors that extends linearly along the longitudinal axis of the distal end portion of the lead.

7. The lead of claim 1, wherein the mid portion comprises a lumen and the distal end portion is a solid cylinder without a lumen.

8. The lead of claim 1, wherein the mid portion has an outer diametric dimension of greater than or equal to 1.25 millimeters.

9. The lead of claim 1, wherein the mid portion and the proximal portion have uniform outer diametric dimensions along their respective lengths, and wherein the diametric dimensions of the mid portion and the proximal portions are the same.

10. A method for manufacturing a lead according to claim 5, comprising:
    extending, in a linear manner each of the more than one conductors from a proximal portion of the distal end portion to one of the electrodes;
    electrically coupling each of the more than one electrodes to one of the electrodes; and
    embedding the more than one conductors in polymeric material such that no luminal void exists between the more than one conductors.

11. The method of claim 10, wherein embedding the conductors in polymeric materials comprises flowing the polymeric material around the one or more conductors.

12. The method of claim 10, wherein the outer diameter of the portion of the lead in which each of the conductors is linearly extended is less than 1 millimeter and wherein said portion has a length of at least 10 millimeters.

13. A method for manufacturing a lead according to claim 6, comprising:
    extending, in a linear manner, each of the more than one individually insulated conductors from a proximal portion of the distal end portion to one of the electrodes;
    braiding the more than one linearly extended individually insulated conductors around each other;
    electrically coupling each of the more than one electrodes to one of electrodes; and
    embedding the more than one individually insulated conductors in polymeric material such that no luminal void exists between the more than one individually insulated conductors.

14. A method comprising:
    inserting a distal end portion of a lead into parenchymal tissue of a brain, wherein the distal end portion of the lead that is inserted into a brain has an outer diameter of 1 millimeter or less and a length of 2 millimeters or more;
    anchoring a mid portion of the lead at a burr hole in a skull, the mid portion of the lead having an outer diameter of greater than 1 millimeter,
    wherein the mid portion is immediately proximal to the distal end portion, and
    wherein the distal end portion of the lead has a length of 20 millimeters or more and accounts for 90% or more of the lead that is inserted into the parenchymal tissue when the lead is properly positioned in the brain, and wherein the distal end portion is the only portion extending distally from the mid portion.

15. The method of claim 14, wherein the distal end portion of the lead has an outer diameter of 0.7 millimeters or less.

16. The method of claim 14, wherein the mid portion of the lead has an outer diameter of 1.25 millimeters or greater.

17. The method of claim 14, wherein the distal end portion of the lead comprises one or more electrodes that are electrically connected to one or more contacts at a proximal end portion of the lead.

18. The method of claim 17, further comprising operably coupling the one or more contacts at the proximal end portion of the lead to an electrical signal generator, and applying an electrical signal generated by the signal generator to the a target region of the brain via the one or more electrodes.

* * * * *